United States Patent
Wilkinson

(10) Patent No.: US 10,496,798 B2
(45) Date of Patent: Dec. 3, 2019

(54) SYSTEMS AND METHODS FOR PROVIDING MEAL PLANS

(71) Applicant: Walmart Apollo, LLC, Bentonville, AR (US)

(72) Inventor: Bruce Walter Wilkinson, Rogers, AR (US)

(73) Assignee: Walmart Apollo, LLC, Bentonville, AR (US)

( * ) Notice: Subject to any disclaimer, the term of this patent is extended or adjusted under 35 U.S.C. 154(b) by 668 days.

(21) Appl. No.: 15/173,298

(22) Filed: Jun. 3, 2016

(65) Prior Publication Data
US 2016/0357942 A1 Dec. 8, 2016

Related U.S. Application Data

(60) Provisional application No. 62/171,150, filed on Jun. 4, 2015.

(51) Int. Cl.
*G16H 20/60* (2018.01)
*G06F 19/00* (2018.01)

(52) U.S. Cl.
CPC .............................. *G06F 19/3475* (2013.01)

(58) Field of Classification Search
CPC ..... G06Q 30/02; G06Q 30/0631; G16H 20/60
See application file for complete search history.

(56) References Cited

U.S. PATENT DOCUMENTS

| | | | |
|---|---|---|---|
| 2002/0046060 A1 | 4/2002 | Hoskyns | |
| 2007/0141540 A1 | 6/2007 | Borg | |
| 2008/0086374 A1 | 4/2008 | Aitken | |
| 2009/0181131 A1 | 7/2009 | Forbes-Roberts | |
| 2009/0259687 A1 | 10/2009 | Do et al. | |
| 2010/0292998 A1 | 11/2010 | Bodlaender | |
| 2011/0055044 A1* | 3/2011 | Wiedl | G06Q 30/02 705/26.5 |
| 2014/0149239 A1* | 5/2014 | Argue | G06Q 30/0631 705/21 |
| 2014/0172894 A1 | 6/2014 | Argue et al. | |
| 2016/0357941 A1 | 12/2016 | Wilkinson | |
| 2016/0379288 A1 | 12/2016 | Wilkinson et al. | |
| 2016/0379320 A1 | 12/2016 | Wilkinson | |
| 2017/0024798 A1 | 1/2017 | Richards et al. | |
| 2018/0165747 A1 | 6/2018 | Patten et al. | |

OTHER PUBLICATIONS https://realfood.tesco.com/meal-planner/create-meal-plan.html.

* cited by examiner

*Primary Examiner* — John A Pauls
(74) *Attorney, Agent, or Firm* — Patterson Thuente Pedersen, P.A.

(57) ABSTRACT

A system ingests the purchases of a user at various retail outlets and are analyzed to characterize a user's taste profile as well as the complexity and effort of meals prepared by the user. A meal plan including the preparation of recipes corresponding to the user's taste, complexity, and effort profiles. Meal plan media including instructions for preparing the meals of the meal plan are provided. Interactions or lack thereof and the date of interactions are monitored and analyzed to determine whether a meal was executed and the date of execution. A weekly schedule profile of the user is developed based on the complexity and effort scores of meals and the determination of whether the meals are or are not executed. Subsequent meal plans are generated based on the schedule profile and the taste profile updated per determinations of which meals are executed.

20 Claims, 7 Drawing Sheets

SYSTEMS AND METHODS FOR PROVIDING MEAL PLANS

CROSS-REFERENCE TO RELATED APPLICATIONS

This application claims the benefit of U.S. Provisional Patent Application 62/171,150, filed Jun. 4, 2015, and titled "Systems And Methods For Providing Meal Plans", the entire contents of which are hereby incorporated herein by reference.

BACKGROUND

Field of the Invention

This invention relates to systems and methods for developing meal plans for a customer.

Background of the Invention

Cooking delicious meals from basic ingredients is a great way to eat healthy. Trying out new recipes and enjoying the results is also enjoyable for many people. For people that work long hours or have small children, it may be difficult to find the time to buy fresh ingredients, even if one has the time to actually cook the meal. Likewise, it may take considerable time to review cooking magazines or recipe websites in order to find new recipes to try. A person may need to actually make many recipes before finding one that actually is suitable for the person's tastes.

The systems and methods described herein below provide an engine that generates meal recommendations for a user that have a high probability of satisfying both a user's tastes and schedule.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which.

DETAILED DESCRIPTION

Figure 1:
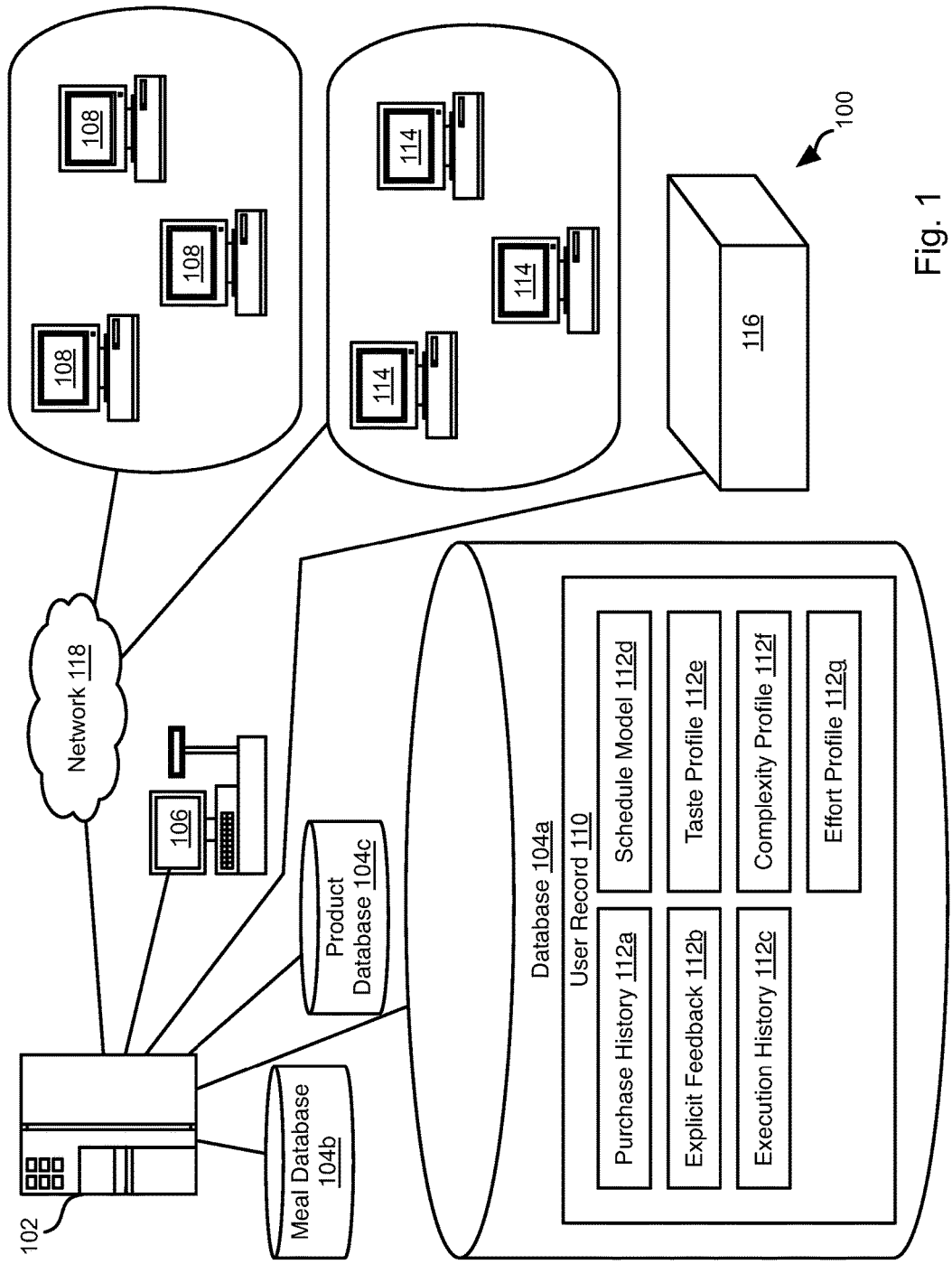
FIG. 1 is a schematic block diagram of a network environment suitable for implementing methods in accordance with embodiments of the invention.

It will be readily understood that the components of the present invention, as generally described and illustrated in the Figures herein, could be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

Embodiments in accordance with the present invention may be embodied as an apparatus, method, or computer program product. Accordingly, the present invention may take the form of an entirely hardware embodiment, an entirely software embodiment (including firmware, resident software, micro-code, etc.), or an embodiment combining software and hardware aspects that may all generally be referred to herein as a "module" or "system." Furthermore, the present invention may take the form of a computer program product embodied in any tangible medium of expression having computer-usable program code embodied in the medium.

Any combination of one or more computer-usable or computer-readable media may be utilized. For example, a computer-readable medium may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. In selected embodiments, a computer-readable medium may comprise any non-transitory medium that can contain, store, communicate, propagate, or transport the program for use by or in connection with the instruction execution system, apparatus, or device.

Computer program code for carrying out operations of the present invention may be written in any combination of one or more programming languages, including an object-oriented programming language such as Java, Smalltalk, C++, or the like and conventional procedural programming languages, such as the "C" programming language or similar programming languages. The program code may execute entirely on a computer system as a stand-alone software package, on a stand-alone hardware unit, partly on a remote computer spaced some distance from the computer, or entirely on a remote computer or server. In the latter scenario, the remote computer may be connected to the computer through any type of network, including a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions or code. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a non-transitory computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

Referring to FIG. 1, a network environment 100 may be used to implement methods as described herein. The environment 100 may include a server system 102 associated with a corporate parent or controlling entity having one or more retail establishments associated therewith. The server system 102 may host or access a database 104a of user data, a meal database 104b, and a product database 104c, which are described in greater detail below. The retail establishments may house point of sale devices (POS) 106 on which transactions may be concluded. The POS 106 may also be part of an e-commerce system. The e-commerce system may include, for example, a web-application that permits customers to purchase various products and/or services over the Internet. POSs 106 in communication with the server system 102 may include POSs 106 associated with a warehouse store that is a separate entity or format than the retail establishments.

Online POSs 106 may interact with remote user computers 108. In particular, server system 102 may host a website that may be browsed by users on the user computers 108 and through which the users may invoke purchase and shipment of products in a product data base 104c.

Records of transactions may be transmitted to the server system 102 by the POSs 106 at one or more outlets, e.g. retail establishments, warehouse stores, and ecommerce systems. The records of various transactions from the various outlets may be associated to individual customers. Specifically, unique data such as a credit card number, address, username, membership number, and the like may be associated with a particular customer. Accordingly, transaction records including one or more items of this unique data may be associated with that user. For example, transaction records determined to be associated with a particular user may be stored in a user record 110 for that user in the database 104a, such as in a purchase history 112a of the user record 110.

The user record 110 for that user may further include records of other information received from a user or gathered from observation of user actions. For example, the user record 110, may include explicit feedback 112b, an execution history 112c, a schedule model 112d, a taste profile 112e, a complexity profile 112f, and an effort profile 112g. The manner in which the data 112b-112g is obtained and used is described in greater detail below.

In some embodiments, one or more users may operate as meal planners providing one or both of meals and recipes for dishes to be included in meals. Such "meal plan generators" may use generator computers 114 and communicate with the server system 102 to provide meals and/or recipes, which are then stored by the server system 102 in the meal database 104b. The meal plan generator may designate access restrictions for the meals and/or recipes as described in greater detail below. The server system 102 may transmit feedback to the generator computers 114 based on usage of the meals and/or recipes, as described in greater detail below.

In some embodiments, deliveries of ingredients for meals defined according to the methods described herein may be automatically identified and delivered according to the method described herein. In some embodiments a smart crate 116 may include computer components such that the smart crate 116 may establish a network connection to the server system 102 for uploading information into the smart crate 116 as described in greater detail below.

The server system 102 may be in data communication with the POSs 106, user computers 108, generator computers 114, and smart crate 116 by means of a network 118 or directly connected thereto. The network 118 may include any wired or wireless connections and may include some or all of a local area network (LAN), wide area network (WAN), the Internet, or other type of network.

Figure 2:
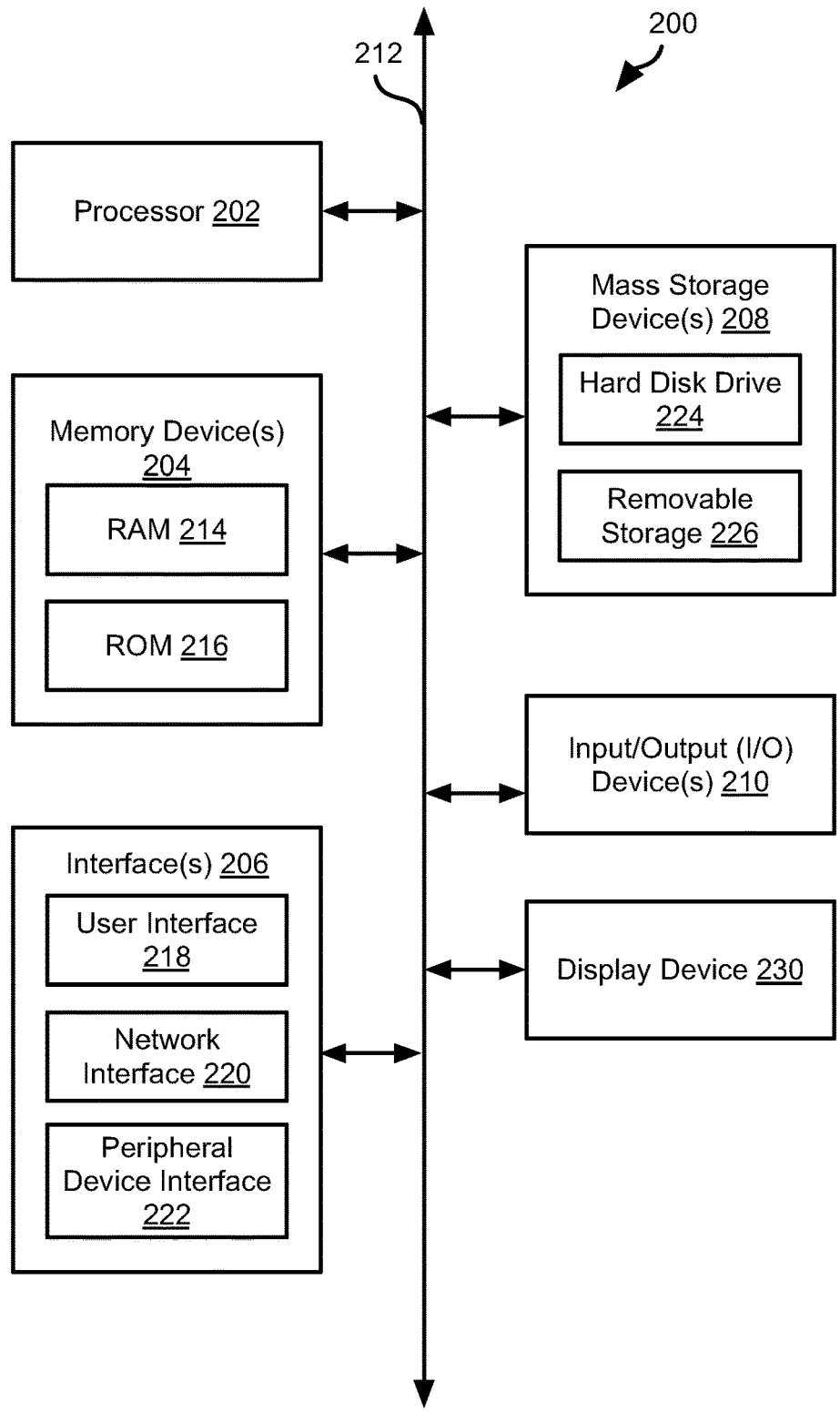
FIG. 2 is a schematic block diagram of an example computing device suitable for implementing methods in accordance with embodiments of the invention.

FIG. 2 is a block diagram illustrating an example computing device 200. Computing device 200 may be used to perform various procedures, such as those discussed herein. The server system 102, user computers 108, generator computers 114, and smart crate 116 may have some or all of the attributes of the computing device 200. Computing device 200 can function as a server, a client, or any other computing entity. Computing device can perform various monitoring functions as discussed herein, and can execute one or more application programs, such as the application programs described herein. Computing device 200 can be any of a wide variety of computing devices, such as a desktop computer, a notebook computer, a server computer, a handheld computer, a tablet computer and the like. A server system 102 may include one or more computing devices 200 each including one or more processors.

Computing device 200 includes one or more processor(s) 202, one or more memory device(s) 204, one or more interface(s) 206, one or more mass storage device(s) 208, one or more Input/Output (I/O) device(s) 210, and a display device 230 all of which are coupled to a bus 212. Processor(s) 202 include one or more processors or controllers that execute instructions stored in memory device(s) 204 and/or mass storage device(s) 208. Processor(s) 202 may also include various types of computer-readable media, such as cache memory.

Memory device(s) 204 include various computer-readable media, such as volatile memory (e.g., random access memory (RAM) 214) and/or nonvolatile memory (e.g., read-only memory (ROM) 216). Memory device(s) 204 may also include rewritable ROM, such as Flash memory.

Mass storage device(s) 208 include various computer readable media, such as magnetic tapes, magnetic disks, optical disks, solid-state memory (e.g., Flash memory), and so forth. As shown in FIG. 2, a particular mass storage device is a hard disk drive 224. Various drives may also be included in mass storage device(s) 208 to enable reading from and/or writing to the various computer readable media. Mass storage device(s) 208 include removable media 226 and/or non-removable media.

I/O device(s) 210 include various devices that allow data and/or other information to be input to or retrieved from computing device 200. Example I/O device(s) 210 include cursor control devices, keyboards, keypads, microphones, monitors or other display devices, speakers, printers, network interface cards, modems, lenses, CCDs or other image capture devices, and the like.

Display device 230 includes any type of device capable of displaying information to one or more users of computing device 200. Examples of display device 230 include a monitor, display terminal, video projection device, and the like.

Interface(s) 206 include various interfaces that allow computing device 200 to interact with other systems, devices, or computing environments. Example interface(s) 206 include any number of different network interfaces 220, such as interfaces to local area networks (LANs), wide area networks (WANs), wireless networks, and the Internet. Other interface(s) include user interface 218 and peripheral device interface 222. The interface(s) 206 may also include one or more peripheral interfaces such as interfaces for printers, pointing devices (mice, track pad, etc.), keyboards, and the like.

Bus 212 allows processor(s) 202, memory device(s) 204, interface(s) 206, mass storage device(s) 208, I/O device(s) 210, and display device 230 to communicate with one another, as well as other devices or components coupled to bus 212. Bus 212 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 200, and are executed by processor(s) 202. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

Figure 3:
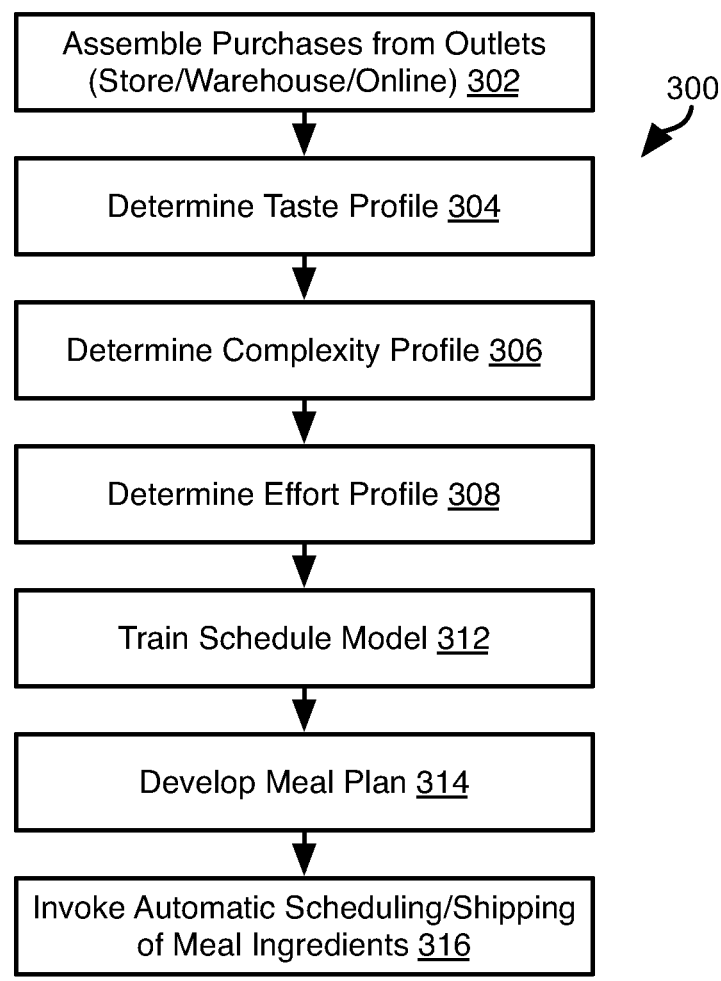
FIG. 3 is a process flow diagram of a method for generating an initial meal plan based on a user purchase history in accordance with an embodiment of the present invention.

Turning now to FIG. 3, the illustrated method 300 may be executed by the server system 102 with respect to each user record 110 of a plurality of user records, the user record representing a specific customer, family, or other entity.

The method 300 may include assembling 302 purchase records for the user of the user record from one or more outlets (e.g., retail, warehouse, online). As noted above, transaction records may be associated to a user due to their inclusion of identifying information unique to the user (username, credit card number, address, phone number, email address, account number, etc.). The transaction records assembled may be stored in a purchase history 112a of the user record for the user.

The method 300 may further include determining 304 a taste profile of the user. For example, each transaction may include a listing of product identifiers. The method 300 may include mapping product identifiers or groups of product identifiers to a particular type of food. For example, product identifiers for tortillas, salsa, cilantro, limes, etc. may correspond to Mexican food. Product identifiers for soy sauce, bean sprouts, etc. may correspond to Chinese food. Of course, some ingredients may be used in multiple styles of cooking, such as cilantro, which may be used in both Mexican and Chinese food. Accordingly, determining 304 a taste profile may include identifying groups of ingredients in the same or different transaction that overlap with a grouping of ingredients corresponding to a particular style of food. The style of food having the greatest number of products of a transaction included in its grouping of ingredients as opposed to other styles of food may be determined to be the style of food for that transaction. The style of food preference may be determined for each transaction or based on an aggregation of products for a plurality of transactions. For example, each transaction, or a group of transactions that are temporally proximate (e.g. within 5, 10, 15, or N days apart), may be analyzed and a style of food identified therefore. The styles of foods identified for a plurality of transactions or plurality of groups of transactions may be determined. The top M styles of foods, e.g. having the top M greatest numbers of transactions or groups of transactions mapped thereto may be selected as the customer's preferred styles of food. Attributes of meals determined from the ingredients may further include values of aesthetics, nutritional value, health benefits, and the like. Any methods known in the art may be used to determine 304 a user's taste preference based on past purchases.

The method 300 may include determining 306 the complexity profile of the user for the user record 110. The complexity profile 306 may indicate the complexity of food prepared by the user. For example, a low complexity food may be a prepared food that need only be heated prior to consumption. A high complexity food may include basic ingredients that must be prepared by the user prior to consumption. Product records may have complexities associated therewith: a microwave dinner may have a low complexity score, flour may have a high complexity score since it must be cooked with other ingredients prior to consumption.

Complexity scores may be determined by identifying groupings of ingredients used to prepare a particular recipe and a complexity of that recipe. For example, a transaction including tomatoes, basil, onions, etc. may indicate a user is making a homemade marinara sauce. Accordingly, the complexity of that transaction may correspond to the complexity of making marinara sauce. The groupings of ingredients for a recipe and the complexity score thereof may be the result of human inputs and stored for use in identifying recipes that may be associated with a transaction and the complexity score for that recipe. A complexity score may be a numerical value with a low value indicating low complexity and a high value indicating high complexity, or vice versa.

The complexity profile of a user may include assigning scores for each of a plurality of complexity ranges. For example, each transaction may be assigned one or more complexity scores indicating whether products of that transaction correspond to a particular complexity. For example, one group of ingredients may indicate a complex dish whereas another item of the same transaction may be a low complexity prepared meal. Accordingly, the transaction may be assigned two complexity scores, one high complexity score and one low complexity score.

The complexity scores of the transactions may be aggregated. For a particular complexity range, the complexity profile may indicate a number or frequency with which transactions having a complexity in that score occur for that user. Other statistical methods may be used to characterize the most common or likely complexity of a user based on the complexity of recipes identified for transactions.

The method 300 may further include determining 308 an effort profile of the user associated with the user record 110. Effort may indicate the time required to prepare a meal whereas complexity indicates the level of skill and the degree of transformation required before an ingredient or group of ingredients may be consumed. As for determining 306 the complexity profile, the effort associated with a particular ingredient, group of ingredients, or product of a transaction may be determined 308 and one or more effort scores assigned to the transaction. As for complexity, recipes including listings of ingredients and a degree of effort may be received from human inputs or other means. Transactions including all or substantially all of the ingredients of a recipe may be assigned the effort score for that recipe. The one or more effort scores of one or more transactions may be aggregated. The effort profile of a user may include a score for a range of effort values indicating the number or frequency of transactions having effort scores in that range. Other statistical measures may also be used to determine from the effort scores of the plurality of transactions, the likelihood of a user preparing a meal for within a given range of effort values.

The method 300 may include training 312 a schedule model for the user according to one or both of the complexity scores and the effort scores of transactions of the user. In particular, training 312 the schedule model may include determining an association between a given day of the week or month and the complexity and/or effort of meals determined to be likely cooked on that day of the week or month.

In many instances, a weekly or bi-weekly shopping trip including a large number of ingredients representing meals of multiple complexities may not necessarily indicate the complexity of a meal for a particular day. However, various methods may be used to identify complexities and effort for meals on a given day of the week. For example, for perishable ingredients, the date of a meal including them may be determined to be within P days from the data of purchase, where P is the life of the product. Where a transaction includes exclusively ingredients for a particular recipe then it may be assumed that a meal including those ingredients is performed on the day of purchase or the day after purchase, e.g. the shopping trip was exclusively for the purpose of shopping for that meal.

Accordingly, the presumed dates of meals and the complexities and efforts of meals as determined from transaction data as described above may be input to a machine learning or other engine that associates a probability of a meal with a given complexity and effort being performed on a particular day of the week. In particular, a set of data points having fields <weekday>, <complexity>,<effort> may be obtained from transaction data where <weekday> is the assumed day of the week for the ingredients of a transaction and <complexity> and <effort> are the complexity and effort for the transaction. These data points are then used to train the schedule model to output a probability of complexity and effort given a weekday as an input.

In addition to the automated training of some or all of the taste, complexity, and effort profiles and the schedule model, explicit inputs of the user may be requested and received. For example, the user may explicitly instruct the server system as to preferred attributes of meals, including any of the attributes noted herein.

The method 300 may further include developing 314 a meal plan for the user associated with the user record 110. In particular, meal plans that include some or all of the style of foods and ingredients according to the taste profile of the user may be selected. The recipes and meals of the meal plan may further be selected to have complexities and efforts conforming to the complexity and effort profiles and schedule model of the user. For example, the complexity and effort of meals scheduled for a weekday may conform to the complexity and effort value for that weekday as determined by the schedule model. Where the schedule model does not indicate, or does not indicate with sufficient confidence, a complexity level for a particular day of the week, the complexity of meals of the meal plan may be selected such that the probability of a meal or recipe of a given complexity being selected is determined based on the complexity profile, i.e. the probability of a meal of a given complexity and effort being included in a meal plan may be proportional to the score for that range of complexity and effort values in the complexity profile.

The method 300 may further include invoking 316 automatic scheduling and shipping of meal ingredients. In particular, the meal plan may include meals for each day, each meal including one or more recipes. The ingredients for a particular meal on a particular day, may be shipped to the user prior to the mealtime associated with that meal. In particular, a picklist may be generated that lists the ingredients to be retrieved and other data required to invoke shipping of a package including the ingredients may automatically be generated. In some embodiments, the ingredients may be shipped in a smart crate 116 as described in U.S. application Ser. No. 14/052,102 filed Oct. 11, 2013, and entitled SECURE DELIVERY RECEPTACLE.

Figure 4:
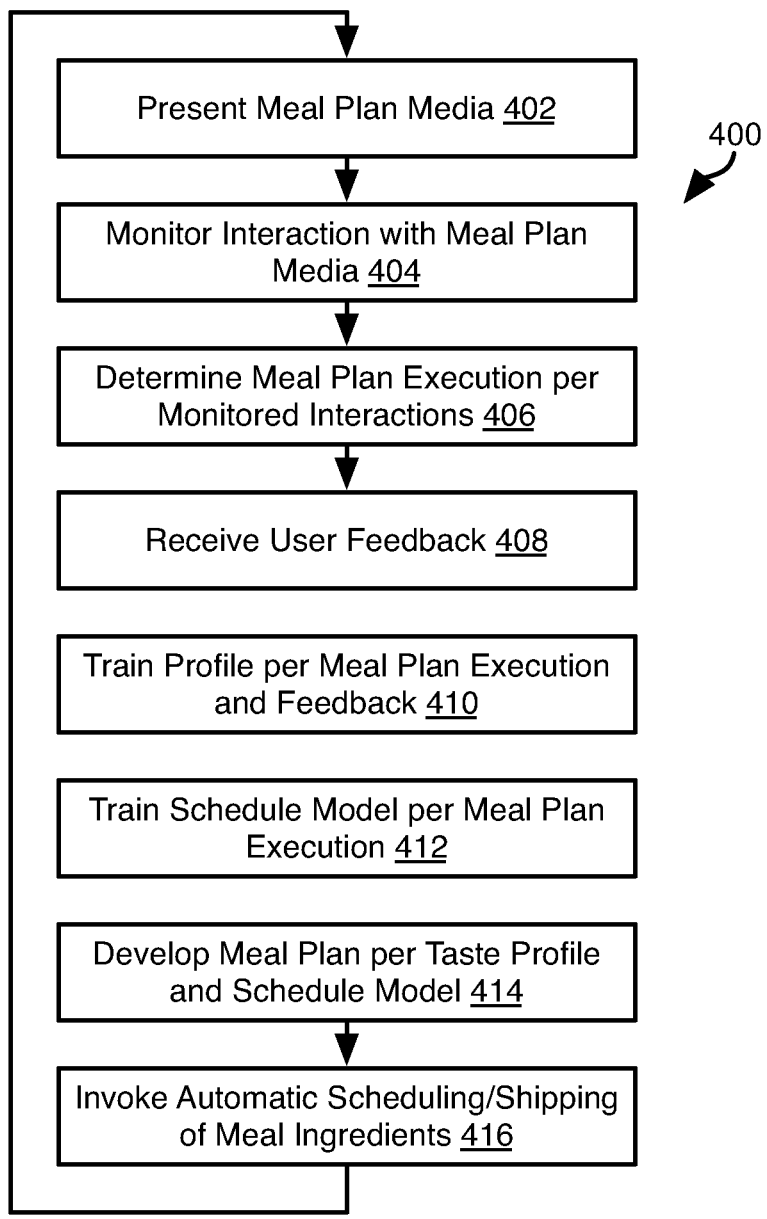
FIG. 4 is a process flow diagram of a method for updating a meal plan based on user behavior in accordance with an embodiment of the present invention.

FIG. 4 illustrates an example method 400 that may be used to update the profiles of a user (taste, complexity, and effort profiles and schedule model). The method 400 may be executed by the server system 102 with respect to a meal of a meal plan. The method 400 may include presenting 402 meal plan media to the user. For example, for a meal generated according to a meal plan, human generated content instructing the preparation of that meal may be accessible to the server system. Content may include videos demonstrating cooking, audio instructions, slide shows of the meal at various stages, textual instructions, and the like. Accordingly, for a meal of a meal plan scheduled for a meal of a specific day, the meal plan media for that meal may presented at some point prior to that meal on that day. Presenting the meal plan media may include transmitting a link thereto to the user in an email, text message, or some other messaging medium. Presenting the meal plan media may include transmitting to a user computer 108 of the user data sufficient to output the meal plan media on the user computer 108.

The method 400 may further include monitoring 404 interactions with the meal plan media. For example, meal plan media may be presented in an interface that monitors user inputs received to, for example, invoke playback of the meal plan media, pause playback of the meal plan media, replay meal plan media, rewind (e.g. return to an earlier point in) the meal plan media. These inputs may be transmitted or analyzed and the result of this analysis transmitted to the server system 102. In particular, the server system 102 or a module executing on the user computer 108 may determine one or more parameters such as how long the meal plan media was presented on the user computer 108, a span of time over which interactions with the meal plan media were received, a number of times the meal plan media was paused or rewound, and a number of times the meal plan media was played (if any). The server system 102 may then determine 406 whether the meal of the meal plan was actually executed. For example, if the meal plan media for a meal (or individual recipe) is determined not to have been played back, then that meal (or individual recipe) may be determined with high certainty not to have been executed. If the meal plan media of a meal (or recipe) was presented with no interruptions or interactions (pause, rewind, replay) then the meal (or recipe) may be determined with a first amount of certainty to have been executed. If the meal plan media of a meal (or recipe) was presented with some interruptions or interactions (pause, rewind, replay) then the meal (or recipe) may be determined with a second amount of certainty to have been executed, with the second amount being greater than the first amount and increasing with the number of interruptions or interactions.

The amount of certainty that a meal was executed (e.g., zero, the first amount, or the second amount as discussed above) may be associated with each meal (or recipe of the meal plan) or a meal (or recipe) may simply deemed to be executed or non-executed based on the interactions. For example, where no viewing occurred, the meal (or recipe) may be deemed non-executed. For viewing with no interactions, the meal (or recipe) may be deemed non-executed in some embodiments, or executed in other embodiments. For viewing with additional interactions, the meal (or recipe) may be deemed executed.

The method 400 may further include receiving 408 user feedback on meals of the meal plan, which may include feedback on individual recipes of the meal plan. In other embodiments, no explicit feedback is solicited or accepted. In some embodiments, only simple feedback is solicited and received ("did you like the meal (yes or no)"). In other embodiments, a degree of enjoyment of the meal may be solicited and received ("how would you rate the meal from 1 to 5"; "how often would you like to prepare this meal"). Receiving 408 feedback, may include transmitting any of these types of requests for feedback to the user computer 108 of the user and receiving any response from the user computer 108.

The method 400 may further include performing further training 410, 412 of the profiles 112e-112g of the user and schedule model 112d by the server system 102. In particular, each meal may have attributes associated therewith including the ingredients used, the style of food (Mexican Chinese, Italian, etc.), the degree of complexity, aesthetics, nutritional values, compliance with a dietary limit (vegan, gluten free, etc.), low calorie, health benefits, the degree of effort, or other attributes, including any attribute of a meal discussed herein. Accordingly, using these attributes and the execution or non-execution of the meal as inputs, a machine learning model may be trained 410 that will output for a given meal with a given set of attributes, the likelihood that the meal will be executed. In particular, the taste, complexity, and effort profiles of the user may be trained in this manner. Alternatively, a single model may be trained according to all of the above-noted attributes such that separate taste, complexity, and effort profiles 112e-112g are not used. The single model will then output for a given set of meal attributes, including those related to taste, complexity, and effort, the likelihood that that meal will be executed. As a result of the training, first meals having attributes (style, ingredients, complexity score, effort score) more similar to meals that are determined to have been executed than second meals will be favored for inclusion in a meal plan over the second meals. Second meals having attributes similar to meals that are determined not to have been executed will be disfavored for inclusion in a meal plan over first meals that have attributes less similar to the meals determined not to have been executed.

Training 412 the schedule model may be performed in a similar manner to step 410. The model may be trained as a machine learning engine that takes as inputs data points that each include a day of the week, the complexity and effort scores of a meal that was scheduled for that day of the week, and whether the meal was executed. In some instances, a user may switch the meal plan such that a meal is executed on a different day than dictated by the meal plan. Accordingly, the day of the week the meal was actually executed, its complexity and effort scores, and the fact that the meal was actually executed may be a data point. In some embodiments, the day of the week the meal was scheduled, its complexity and effort scores, and the fact that the meal was not executed on that day may also be a data point. The machine learning engine may train a model using these data points that outputs for a given day of the week, the complexity and effort score that is likely to be executed on that day. Alternatively, the machine learning engine may train a model using these data points that outputs for a given complexity and effort scores of a meal and day of the week, the likelihood that a meal having that complexity and effort score will be executed. In either case, meals that have first complexity and effort scores that are closer to the complexity and effort scores of meals that are determined to have been executed on a given week day will be favored for inclusion in a meal plan for execution on that week day. Meals that have second complexity and effort scores that further from the complexity and effort scores of meals that are determined to have been executed on a given week day than the first complexity and effort scores will be disfavored for inclusion in a meal plan for execution on that week day. Stated differently, the probability of a meal being scheduled for a given week day increases with similarity of the complexity and effort scores of that meal to the complexity and effort scores of meals determined to have been executed on that day.

The method 400 may further include developing 414 by the server system 102 an updated meal plan according to the taste profile and schedule model as updated at steps 410 and 412. In particular, from a corpus of meals or recipes having complexity and effort scores and taste attributes associated therewith, a set of meals may be defined that satisfies both the taste profile of the user and have the appropriate complexity and effort requirements for the schedule of the user. In particular, a meal selected for a given day of the week may have a complexity and effort score conforming to that indicated by the schedule model as trained at step 410. In some embodiments, the meal plans may include meals selected to provide a degree of variety, e.g. ensuring that meals on consecutive days are of different styles or have a number of ingredients that are not common to each meal.

The ingredients for each meal of the meal plan developed at step 414 may then be invoked 416 as described above. In particular, shipment of the ingredients for a meal in the meal plan may be invoked such that they arrive at the home of the user prior to the scheduled date and time of the meal, e.g. the day of the meal at least an hour or some other interval before the conventional time of the meal.

Figure 5:
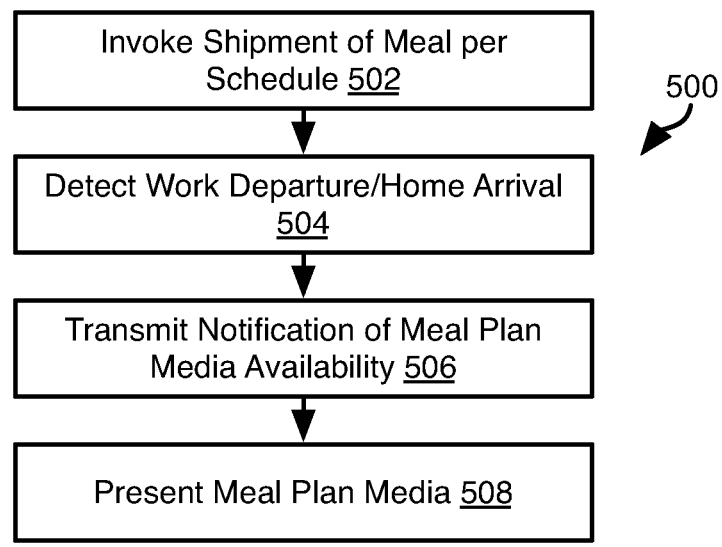
FIG. 5 is a process flow diagram of a method for providing access to a meal plan in accordance with an embodiment of the present invention.

The illustrated method 500, shown in FIG. 5, may be executed by the server system 102 in order to deliver ingredients of a meal at an appropriate time, the meal being a meal from a meal plan generated as described hereinabove. The method 500 may include invoking 502 shipment of the ingredients of a meal according to a meal plan, e.g. on the day in which the ingredients are to be used according to the meal plan. In response to the invoking 502 of shipment, the method 500 may include detecting 504 the user for whom the meal plan was developed one of (a) departing from work or (b) arriving home. Detecting 504 departure or arrival may be performed by a user computer 108 embodied as a mobile device having a global positioning system (GPS) receiver. An application executing on the user computer 108 may store locations defined as one or both of the user's place of work or home. The application may then transmit a notification to the server system 102 upon the location of the user computer 108 transitioning away from a threshold proximity to the user's place of work or transitioning to within a threshold proximity to the user's home.

In response to detecting departure from work or arrival at home, the method 500 may include transmitting 506 notification of meal plan media to the user computer 108, which may include the same mobile device used to detect departure or arrival or a different user computer 108, or both. Transmitting 506 notification may include transmitting a text message including a link to the meal plan media or the meal scheduled that day or transmitting data sufficient to playback the meal plan media to the user computer 108. The notification may include pictures, videos, or other content to encourage the user to prepare the meal. The meal plan media may then be presented 508 on the user computer 108 as described above.

Figure 6:
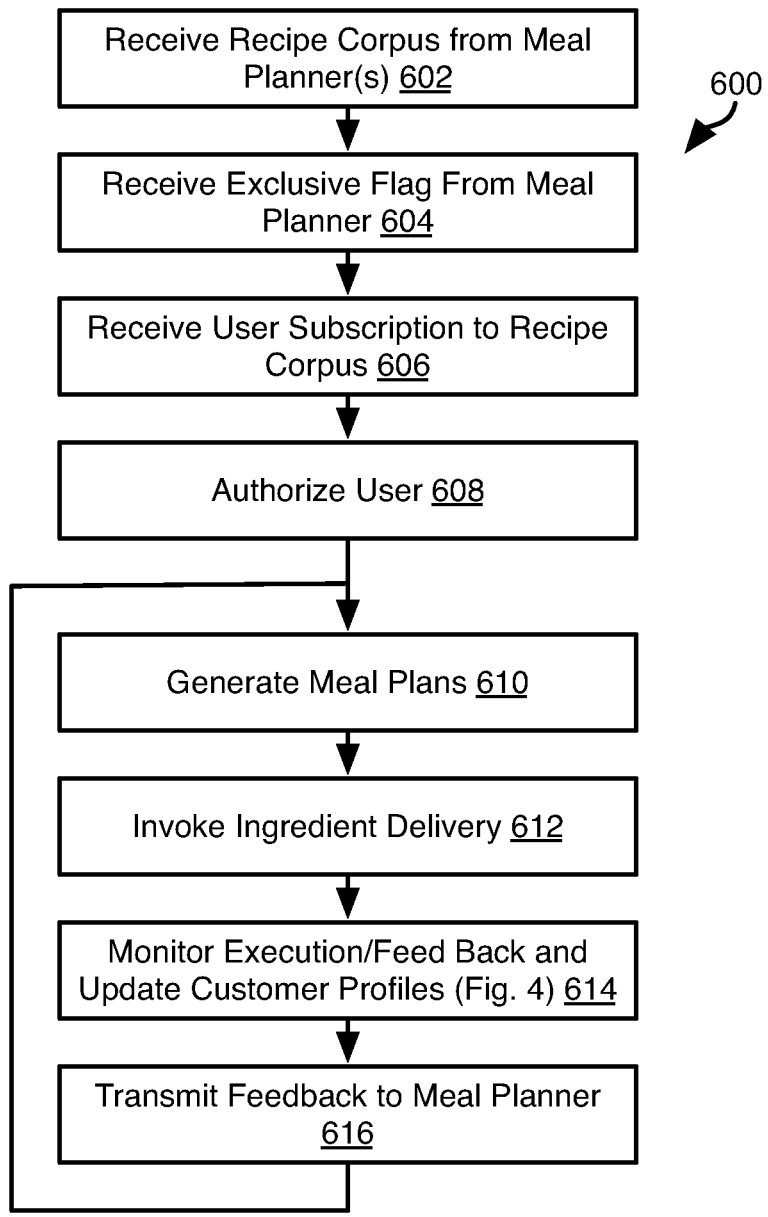
FIG. 6 is a process flow diagram of a method for performing meal recommendations using meals from a third party meal planner in accordance with an embodiment of the present invention.

Referring to FIG. 6, the illustrated method 600 may be used to facilitate provision of meals and/or plans by meal plan generators to users. In the following description and throughout this application, reference to communication with a user may be interpreted as communication with a user computer 108 operated by the user and communication with a meal plan generator may be interpreted as communication with a generator computer 114.

The method 600 may include receiving 602 a recipe corpus from one or more meal planners. The recipe corpus may include a collection of recipes and may further include definitions of groups of recipes for meals. The recipe corpus may further include define groupings of meals for meal plans. The recipes and/or meals may include attributes associated therewith that facilitate selection according to the methods described herein, e.g. complexity and effort scores, a listing of ingredients, a food style (Mexican, Chinese, Italian, etc.). Attributes may further include values of aesthetics, nutritional value, health benefits, and the like. A recipe corpus may have a particular purpose associated therewith, such as complying with a dietary restriction (e.g. gluten free, vegan, etc.) or for a specific purpose (weight loss, athletic performance, building muscle mass, etc.). The recipe corpus may simply be a collection of recipes by an author or entity.

The method 600 may further include receiving 604 an exclusive flag from the meal planner for the recipe corpus received at step 602. The exclusive flag may indicate that the recipe corpus is not available for free to the general public but rather requires a user to provide authentication or otherwise subscribe to the recipe corpus. Receiving 606 and management of subscriptions to the recipe corpus may be performed by the server system 102. For example, the server system 102 may process payment from the user and, in response, submit some or all of the payment to the meal plan generator and provide the user with access, e.g. a username and/or password that when input by the user enable the user to access the recipe corpus. Alternatively, subscriptions may be managed by the meal plan generator, which provides authentication information to the user. The server system 102 may then be provided sufficient information to verify the authentication information or forward the authentication information to the meal plan generator, which instructs the server system 102 to allow or deny access.

Subsequent to the user subscribing to a particular recipe corpus, the user may authenticate with the server system 102, such as by providing a user name and password. Once the user name and password are verified 608 by the server system 102 or the meal plan generator, some or all of the subsequent steps 610-616 may be performed for the user using the recipe corpus. In some embodiments, a user may subscribe to multiple corpuses such that the authorizing step 608 may perform verifying the user's access to the multiple corpuses and steps 610-616 are performed with respect to a combination of recipes from the multiple corpuses.

The method 600 may include generating 610 meal plans, invoking 612 ingredient delivery, and updating the customer profile (taste profile, complexity profile, effort profile, schedule model) according to monitoring 614 of the feedback and execution. Steps 610-614 may be performed in the same manner as described above with respect to FIG. 4 except that the recipes, meals, and/or meal plans are selected from the corpus received at step 602, or multiple corpuses received at step 602.

The method 600 may further include transmitting 616 feedback to the meal plan generator from which the recipe corpus was received 602. Feedback transmitted may include explicit feedback solicited and received as described above with respect to FIG. 4 as well as whether a meal or recipe was determined to have been executed as also described above with respect to FIG. 4. Feedback transmitted 616 to the meal plan generator may include feedback from multiple users and may include a statistical characterization of one or both of explicit feedback and execution or non-execution of recipes and/or meals of the recipe corpus. For example, a percentage of people that were presented a recipe or meal that actually executed it or an average rating of a recipe or meal. Feedback may also indicate the average complexity or effort scores of meals that were or were not executed. A percentage of users who completed meals having a given range of complexity and/or effort scores may also be computed for a plurality of ranges of complexity and/or effort scores. Other statistical characterizations of the attributes of meals described herein and instances of execution or non-execution thereof may also be calculated and provided to the meal plan generator.

Figure 7:
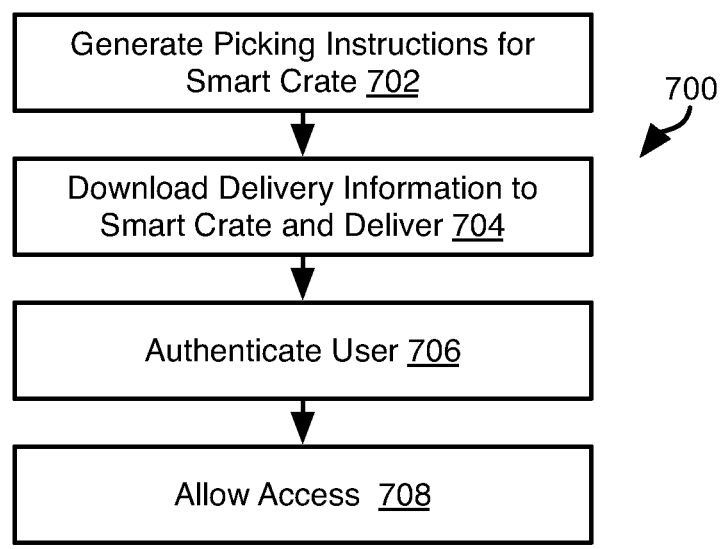
FIG. 7 is a process flow diagram of a method for providing meal ingredients using a smart crate in accordance with an embodiment of the present invention.

Referring to FIG. 7, the illustrated method 700 may be performed in order to facilitate placement of ingredients for a meal in the smart crate 116, where the ingredients are automatically determined from one or more recipes of a meals of a meal plan generated according to the methods described herein.

The method 700 may include generating 702 picking instructions for the smart crate 116. Picking instructions may be instructions output to a display device or input to a robotic retrieval system including sufficient information to retrieve some or all of the ingredients required to execute a meal of a meal plan. The list of ingredients may be extracted from a data record describing the meal and or individual recipes of the meal. The picking instructions may further include information instructing the retrieval of ice or other products to facilitate fresh arrival of the ingredients.

The method 700 may further include downloading 704 delivery information to the smart crate 116. Delivery information may include an address to which the smart crate 116 is to be delivered. Delivery information may further include information enabling the smart crate 116 to verify that a user attempting to access the smart crate 116 is authorized. For example, an authentication code or identifier may be downloaded to the smart crate 116. Upon receipt, a user may authenticate 706 themselves with the smart crate 116. Authentication 706 may include receiving input of a code on a keypad, detecting proximity of a mobile device providing an appropriate authentication code to the smart crate 116, or some other method. Upon verifying that an input code or detected device corresponds to the authentication information downloaded at step 704, the smart crate 116 may then release an electronic lock and allow 708 the smart crate 116 to be opened.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed is:

1. A method for meal plan generation, the method comprising:
   receiving, by a server system, from a first computer associated with a first user a recipe corpus defining a plurality of recipes each having a plurality of attributes;
   receiving, by the server system, from the first user a subscription restriction for the recipe corpus;
   receiving, by the server system, from a second computer associated with a second user a request to access the recipe corpus, the request satisfying the subscription restriction;
   receiving, by a server system, records of purchases for a plurality of products by the second user;
   analyzing, by the server system, attributes of the plurality of products;
   generating, by the server system, a user profile for the second user according to the analyzing of the attributes of the plurality of products;
   generating, by the server system, an initial meal plan including a plurality of meals conforming to the user profile of the second user and including recipes selected from the plurality of recipes of the recipe corpus;
   transmitting, by the server system, the initial meal plan to the second user;
   receiving, by the server system, feedback on the initial meal plan from the second user;
   transmitting, by the server system, the feedback to the first user; and
   training, by the server system, a machine learning model based on the feedback including:
      determining at least one complexity score for each meal in the initial meal plan, the complexity score representing the level of skill and the degree of transformation required to complete a meal,
      determining at least one effort score for each meal in the initial meal plan, the effort score representing the time required to complete a meal; and
   updating, by the server system, and based on the machine learning model, the initial meal plan to create a dynamic meal plan for the user to favor scheduling meals having at least one of a complexity score or an effort score closer to those preferred by the user.

2. The method of claim 1, wherein transmitting the initial meal plan to the second user comprise transmitting menu media including instructions for executing the plurality of meals;
   wherein receiving, by the server system, feedback on the initial meal plan from the second user comprises:
      monitoring, by the server system, accessing of the menu media by the second user;
      updating, by the server system, the user profile of the second user according to the monitoring of accessing of the menu media;
      updating, by the server system, the dynamic meal plan, conforming to the updating of the user profile of the second user; and
      transmitting, by the server system, the dynamic meal plan to the second user.

3. The method of claim 2, wherein monitoring, by the server system, accessing of the menu media further comprises:
   receiving notification of first actions taken with respect to playback of video content in the menu media for a first meal of the plurality of meals of the initial meal plan, the actions including one or more of playing of the video content, pausing of the video content, and one or more additional playbacks of the video content; and
   determining that the actions taken with respect to playback indicate that the menu media for the first meal was executed by the second user.

4. The method of claim 3, wherein monitoring, by the server system, accessing of the menu media further comprises:
   determining that video content in the menu media for a second meal of the plurality of meals has not been the subject of the first actions;
   determining that the second meal was not executed by the second user in response to determining that the video content in the menu media for the second meal has not been the subject of the first actions.

5. The method of claim 4, wherein updating, by the server system, the user profile of the second user according to the monitoring of accessing of the menu media further comprises:
   training the machine learning model to favor meals having attributes of the first meal and disfavor meals having attributes of the second meal, the attributes including the at least one complexity score and the at least one effort score for each meal.

6. The method of claim 4, wherein updating, by the server system, the user profile of the second user according to the monitoring of accessing of the menu media further comprises:
   determining a date of execution of the first meal according to timing of the first actions;
   determining a scheduled execution date for the second meal according to the initial meal plan;
   updating a schedule profile of the user to favor scheduling meals having at least one of complexity scores and effort scores closer to the at least one of the first complexity score and the first effort score than to the at least one of the second complexity score and the second effort score on a weekday corresponding to the date of execution of the first meal; and
   updating the schedule profile of the user to disfavor scheduling meals having at least one of complexity scores and effort scores closer to the at least one of the second complexity score and the second effort score than to the at least one of the first complexity score and first effort score on a weekday corresponding to the scheduled execution date for the second meal.

7. The method of claim 4, wherein updating, by the server system, the user profile of the second user according to the monitoring of accessing of the menu media further comprises:
   determining an estimated date of execution of the first meal according to timing of the first actions;
   determining a scheduled date for the second meal according to the initial meal plan;

updating a complexity profile of the user to favor scheduling meals having at least one of complexity scores and effort scores closer to the at least one of the first complexity score and the first effort score than to the at least one of the second complexity score and the second effort score.

8. The method of claim 4, wherein updating, by the server system, the user profile of the second user according to the monitoring of accessing of the menu media further comprises:
updating a taste profile of the user to favor scheduling meals having ingredients more similar to those of the first meal than those of the second meal.

9. The method of claim 4, wherein transmitting, by the server system, the feedback to the first user further comprises:
transmitting to the first user notification of the execution of the first meal by the second user and non-execution of the second meal by the second user.

10. The method of claim 1, further comprising, for each meal of the plurality of meals of the initial meal plan and dynamic meal plan:
determining ingredients for the each meal; and
invoking shipping of at least a portion of the ingredients for the each meal on a date associated with the each meal.

11. A system for meal plan generation, the system comprising one or more processors and one or more memory devices operably coupled to the one or more processors and storing executable and operational code effective to cause the one or more processors to:
receive from a first computer associated with a first user a recipe corpus defining a plurality of recipes each having a plurality of attributes;
receive from the first computer a subscription restriction for the recipe corpus;
receive from a second computer associated with a second user a request to access the recipe corpus, the request satisfying the subscription restriction;
retrieve from a customer information database records of purchases for a plurality of products by the second user;
analyze attributes of the plurality of products;
generate a user profile for the second user according to the analyzing of the attributes of the plurality of products;
store the user profile for the second user in a user profile database;
generate an initial meal plan including a plurality of meals conforming to the user profile of the second user and including recipes selected from the plurality of recipes of the recipe corpus;
transmit the initial meal plan to the second user;
receive feedback on the initial meal plan from the second user;
transmit the feedback to the first user; and
training a machine learning model based on the feedback including:
determining at least one complexity score for each meal in the initial meal plan, the complexity score representing the level of skill and the degree of transformation required to complete a meal,
determining at least one effort score for each meal in the initial meal plan, the effort score representing the time required to complete a meal; and
updating, based on the machine learning model, the initial meal plan to create a dynamic meal plan for the user to favor scheduling meals having at least one of a complexity score or an effort score closer to those preferred by the user.

12. The system of claim 11, wherein the executable and operational code are further effective to cause the one or more processors to:
transmit the initial meal plan to the second user by transmitting menu media including instructions for executing the plurality of meals;
receive feedback on the meal plan from the second user by:
monitoring, by the server system, accessing of the menu media by the second user;
updating, by the server system, the user profile of the second user according to the monitoring of accessing of the menu media;
updating, by the server system, the dynamic meal plan conforming to the updating of the user profile of the second user and the at least one complexity score and the at least one effort score; and
transmitting, by the server system, the dynamic meal plan to the second user.

13. The system of claim 12, wherein the executable and operational code are further effective to cause the one or more processors to monitor accessing of the menu media by:
receiving notification of first actions taken with respect to playback of video content in the menu media for a first meal of the plurality of meals of the initial meal plan, the actions including one or more of playing of the video content, pausing of the video content, and one or more additional playbacks of the video content; and
determining that the actions taken with respect to playback indicate that the menu media for the first meal was executed by the second user.

14. The system of claim 13, wherein the executable and operational code are further effective to cause the one or more processors to monitor accessing of the menu media by:
determining that video content in the menu media for a second meal of the plurality of meals has not been the subject of the first actions;
determining that the second meal was not executed by the second user.

15. The system of claim 14, wherein the executable and operational code are further effective to cause the one or more processors update the user profile of the second user according to the monitoring of accessing of the menu media by:
training the machine learning model to favor meals having attributes of the first meal and disfavor meals having attributes of the second meal, the attributes including the at least one complexity score and the at least one effort score for each meal.

16. The system of claim 14, wherein the executable and operational code are further effective to cause the one or more processors to update the user profile of the second user according to the monitoring of accessing of the menu media by:
determining a date of execution of the first meal according to timing of the first actions;
determining a scheduled execution date for the second meal according to the initial meal plan;
updating a schedule profile of the user to favor scheduling meals having at least one of complexity scores and effort scores closer to the at least one of the first complexity score and the first effort score than to the at least one of the second complexity score and the second effort score on a weekday corresponding to the date of execution of the first meal; and updating the schedule profile of the user to disfavor scheduling meals having at least one of complexity scores and effort scores closer to the at least one of the second complexity score and the second effort score than to the at least one of the first complexity score and first effort score on a weekday corresponding to the scheduled execution date for the second meal.

17. The system of claim 14, wherein the executable and operational code are further effective to cause the one or more processors to update the user profile of the second user according to the monitoring of accessing of the menu media by:

determining an estimated date of execution of the first meal according to timing of the first actions;

determining a scheduled date for the second meal according to the initial meal plan;

updating a complexity profile of the user to favor scheduling meals having at least one of complexity scores and effort scores closer to the at least one of the first complexity score and the first effort score than to the at least one of the second complexity score and the second effort score.

18. The system of claim 14, wherein the executable and operational code are further effective to cause the one or more processors to update the user profile of the second user according to the monitoring of accessing of the menu media by:

updating a taste profile of the user to favor scheduling meals having ingredients more similar to those of the first meal than those of the second meal.

19. The system of claim 14, wherein executable and operational code are further effective to cause the one or more processors to transmit the feedback to the first user by:

transmitting to the first user notification of the execution of the first meal by the second user and non-execution of the second meal by the second user.

20. The system of claim 11, wherein executable and operational code are further effective to cause the one or more processors to, for each meal of the plurality of meals of the initial meal plan and dynamic meal plan:

determine ingredients for the each meal; and invoke shipping of at least a portion of the ingredients for the each meal on a date associated with the each meal.

\* \* \* \* \*